(12) United States Patent
Shafiee et al.

(10) Patent No.: US 12,235,259 B2
(45) Date of Patent: Feb. 25, 2025

(54) AUTOMATIC DETERMINATION OF A BIOLOGICAL CONDITION OF A SUBJECT FROM FERNING PATTERNS

(71) Applicant: THE BRIGHAM AND WOMEN'S HOSPITAL, INC., Boston, MA (US)

(72) Inventors: Hadi Shafiee, Boston, MA (US); Manoj Kumar Kanakasabapathy, Boston, MA (US); Prudhvi Thirumalaraju, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 724 days.

(21) Appl. No.: 17/290,523

(22) PCT Filed: Nov. 1, 2019

(86) PCT No.: PCT/US2019/059393
§ 371 (c)(1),
(2) Date: Apr. 30, 2021

(87) PCT Pub. No.: WO2020/092901
PCT Pub. Date: May 7, 2020

(65) Prior Publication Data
US 2022/0011291 A1     Jan. 13, 2022

Related U.S. Application Data

(60) Provisional application No. 62/754,247, filed on Nov. 1, 2018.

(51) Int. Cl.
*G01N 33/487* (2006.01)
*G06N 3/04* (2023.01)
(Continued)

(52) U.S. Cl.
CPC ............. *G01N 33/487* (2013.01); *G06N 3/04* (2013.01); *G06T 7/0012* (2013.01); *H04N 23/55* (2023.01);
(Continued)

(58) Field of Classification Search
CPC .................................................... G01N 33/487
See application file for complete search history.

(56) References Cited

U.S. PATENT DOCUMENTS

| 2003/0105731 A1 | 6/2003 | Lapointe et al. |
| 2008/0264152 A1 | 10/2008 | Sullivan |

(Continued)

FOREIGN PATENT DOCUMENTS

| CN | 107714096 A | 2/2018 |
| CN | 107844828 A | 3/2018 |

(Continued)

OTHER PUBLICATIONS

Anonymous: "Fern test—Wikipedia",Dec. 26, 2017 (Dec. 26, 2017), XP055937017, Retrieved from the Internet: URL:https://en.wikipedia.org/w/index.php?t itle=Fern_test&oldid=817176270 [retrieved on Jun. 30, 2022].

(Continued)

*Primary Examiner* — Daniel T Tekle
(74) *Attorney, Agent, or Firm* — Tarolli, Sundheim, Covell & Tummino LLP

(57) ABSTRACT

Systems and methods are provided for determining if a subject has a biological condition from a dried fluid sample. A fluid sample from a subject is dried in a microfluidic device to provide a dried fluid sample. The dried fluid sample is imaged at a camera to provide a sample image, and the sample image is provided to a computer vision mode. At
(Continued)

the computer vision model, it is determined if the sample image contains a ferning pattern indicative of a biological condition of the subject.

17 Claims, 3 Drawing Sheets

(51) Int. Cl.
*G06T 7/00* (2017.01)
*H04N 23/55* (2023.01)
*H04N 23/56* (2023.01)

(52) U.S. Cl.
CPC ... *H04N 23/56* (2023.01); *G06T 2207/20084* (2013.01); *G06T 2207/30041* (2013.01)

(56) References Cited

U.S. PATENT DOCUMENTS

| | | | | |
|---|---|---|---|---|
| 2014/0247972 | A1* | 9/2014 | Wang | G06F 18/214 382/133 |
| 2014/0313322 | A1* | 10/2014 | Denise | G01N 33/487 348/135 |
| 2018/0130203 | A1 | 5/2018 | Abedini et al. | |
| 2018/0368816 | A1* | 12/2018 | Kim | G01N 33/4875 |
| 2019/0188237 | A1* | 6/2019 | Chen | G06N 3/063 |
| 2019/0192122 | A1* | 6/2019 | Bodo | A61B 10/0012 |
| 2019/0261960 | A1* | 8/2019 | Lee | G06T 7/62 |
| 2020/0106932 | A1* | 4/2020 | Chou | H04N 23/51 |

FOREIGN PATENT DOCUMENTS

| | | |
|---|---|---|
| CN | 108152087 A | 6/2018 |
| DK | 201770672 A1 | 10/2018 |
| WO | 2017/087703 A1 | 5/2017 |
| WO | 2018/002678 A1 | 1/2018 |
| WO | 201879916 A1 | 5/2018 |
| WO | 2018079916 A1 | 5/2018 |

OTHER PUBLICATIONS

European Search Report for Corresponding Application Serial No. PCT/US2019059393.
PCT International Search Report and Written Opinion for corresponding International Application Serial No. PCT/US2019/059393, mailed Nov. 1, 2019, pp. 1-15.
Howard, Andrew G., et al. "Mobilenets: Efficient convolutional neural networks for mobile vision applications." arXiv preprint arXiv:1704.04861 (2017).
Duff, Patrick, Charles J. Lockwood, and V. A. Barss. "Preterm premature (prelabor) rupture of membranes." Up to Date (2017).
Canadian Search Report for Corresponding Application Serial No. 3,118,458, Dated Sep. 1, 2022.
Canadian Office Action, dated Apr. 11, 2023, pp. 1-6.

* cited by examiner

AUTOMATIC DETERMINATION OF A BIOLOGICAL CONDITION OF A SUBJECT FROM FERNING PATTERNS

RELATED APPLICATIONS

This application claims priority from U.S. patent application Ser. No. 62/754,247, filed 1 Nov. 2018, which is incorporated herein in its entirety.

TECHNICAL FIELD

This invention relates to medical systems, and more particularly, to automatic determination of a biological condition of a subject from ferning patterns.

BACKGROUND

Family planning reinforces people's rights to determine the number and spacing of their children. The timing of sexual intercourse in relation to ovulation strongly influences the chance of successful conception and can be an effective method for natural family planning. Nearly forty-four percent of all pregnancies worldwide are unplanned or unintended. Unintended pregnancies can have adverse consequences to the health of both mother and child and are subject to significant economic and social burden.

SUMMARY OF THE INVENTION

In accordance with an aspect of the present invention, a system includes an optical assembly comprising at least one lens and having an associated axis. A microfluidic device includes a channel to hold a fluid sample from a subject and is configured to engage with the housing such that the channel is aligned with the axis of the optical assembly. A camera is aligned with the axis of the optical assembly. The system further includes a processor and a non-transitory computer readable medium storing executable instructions for providing at least one image captured at the camera to a computer vision model to determine if there is a ferning pattern representative of a biological condition of the subject in the at least one image.

In accordance with another aspect of the present invention, a method includes drying a fluid sample from a subject in a microfluidic device to provide a dried fluid sample. The dried fluid sample is imaged at a camera to provide a sample image, and the sample image is provided to a computer vision mode. At the computer vision model, it is determined if the sample image contains a ferning pattern indicative of a biological condition of the subject.

In accordance with yet another aspect of the present invention, a system includes an optical assembly comprising at least one lens. A microfluidic chip includes a channel to hold a dried saliva sample from a subject and is configured to engage with the optical assembly such that the reservoir is aligned with the optical axis of the optical assembly. A mobile device includes a camera aligned along the optical axis of the optical assembly, a processor, and a non-transitory computer readable medium storing executable instructions for determining if the subject is ovulating from images captured at the camera. The executable instructions include a camera interface configured to instruct the camera to capture the images, a convolutional neural network that determines if there is a ferning pattern representative of ovulation by the subject in the at least one image, and a user interface that displays the output of the convolutional neural network on a display of the mobile device.

DETAILED DESCRIPTION

Figure 1:
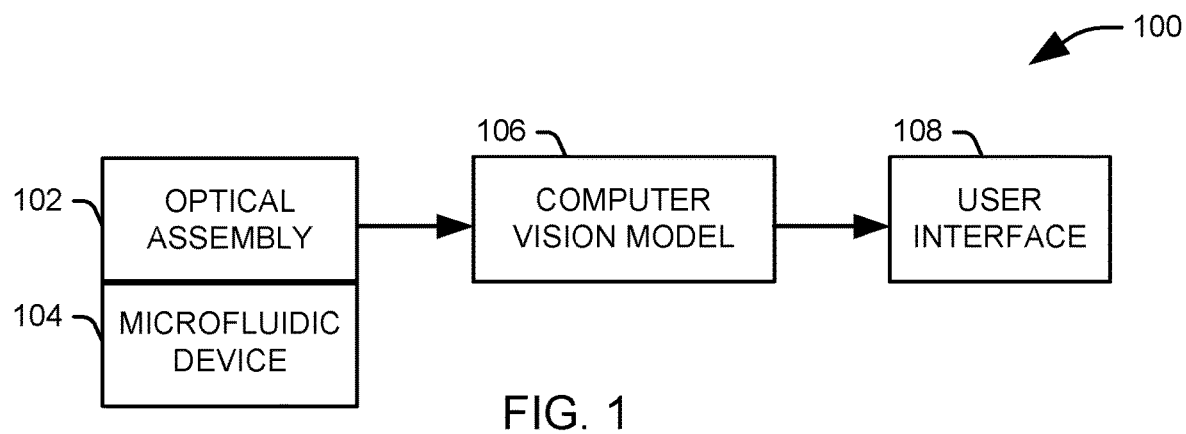
FIG. 1 illustrates an example of a system for automatic determination of a biological condition of a subject from ferning patterns.

In accordance with an aspect of the present invention, a point-of-care system for automatic determination of a biological condition of a subject from ferning patterns is provided. In one example, the system can be used to detect ovulation. Natural family planning uses physical signs, symptoms, and physiologic changes to predict a woman's fertility. Some of the methods for monitoring woman's fertility include ovulation detection through luteinizing hormone (LH) level determination, salivary beta-glucuronidase activity evaluation, rectal or oral basal body temperature analysis, cervical mucus characterization, and salivary ferning analysis. Salivary ferning analysis is relatively inexpensive and simple, making it an attractive alternative to most available approaches.

During the follicular phase of the menstrual cycle, with the increase of estradiol levels in the blood, there is an increase in the salivary electrolytes. This results in consistent ferning appearance, a crystallized structure resembling fern leaves, in air-dried saliva and can be used to determine the ovulation period. Ferning structures have been observed in ovulating women within a four-day window around the day of ovulation. However, current ovulation tests based on salivary ferning are manual and highly subjective, which causes misinterpretation when performed by a lay consumer.

The systems and method disclosed herein can be used for other medical applications that involve imaging of microstructures in an illuminated environment, such as detecting fern structures in amniotic fluid for diagnosing premature rupture of membranes (PROM) in pregnant women and tear film for detecting dry eye disease. Rupture of membranes (ROM) is the breaking of amniotic sac that occurs before the onset of labor. On the other hand, dry eye disease is diagnosed by testing the ocular tear film for fern patterns. Healthy tear samples produce dense fern patterns, which is absent in dry eye samples.

A rapid point-of-care ovulation testing also has an important application in animal breeding. It will be appreciated that the systems and methods disclosed herein are intended for both medical and veterinary use, and that a "subject," as used herein, can refer to a either a human being or an animal. Animal breeding is mainly dependent on the breeding cycle of the species and it is time constrained. One of the important criteria for animal breeding is to determine the optimum time to breed an animal in-order-to achieve higher conception rate. For an egg fertilized later in its maturity, the chances for abortion are greater. Therefore, there is a need for advanced prediction of ovulation. The developed smartphone-based automated optical system can be potentially used for analyzing the saliva ferning patterns in animals such as buffalos, dogs, and other mammals to predict and confirm its ovulation and detect the optimum insemination time. To determine insemination time, many animal breeders rely on manual techniques such as heat indications, but it is not always accurate; ovulation can take place before, during, or after visible heat. Other devices such as electronic pedometers or activity tags are used to detect ovulation by monitoring changes in behavior such as restlessness, standing heat, mounting behavior, and elevated physical activity of animals. Some animals are sensitive to these types of measurements and it becomes difficult for the animal breeders to test them through these methods. To eliminate such complications, a regular, point-of-care, easily available and convenient system for ovulation detection allows for effective management of animal breeding.

The systems and methods provided herein provide a simple, low-cost, and automated device for automatic determination of a biological condition of a subject that uses a computer vision model for the accurate detection of ferning patterns in a small volume of air-dried saliva samples placed on a microfluidic device. A computer vision model, such as a convolutional neural network, is used to rapidly analyze and detect ferning patterns in air-dried saliva samples. In one implementation, utilizing a stand-alone optical assembly configured for use with a smartphone, the system was able to detect ovulation with an accuracy of 99.5% when tested with two hundred images of human saliva collected during the ovulating and non-ovulating phases of the menstrual cycle.

One of the major advantages of the reported approach over all other available methods is its cost effectiveness in the long term. The total material cost for our approach is around fourteen U.S. dollars and is completely reusable. Urine-based tests can range from one or two dollars per test; however, they are not reusable and thus per cycle the overall test can cost approximately thirty-five or forty dollars for a user in the US. According to prior reports most women get pregnant within six cycles, therefore, we estimate that these non-reusable tests can cumulatively cost upwards of two hundred dollars for many women. Furthermore, since at least one implementation of the system can perform all the required analysis on a mobile device without the need for the internet, it is especially attractive for use in resource limited settings.

FIG. 1 illustrates an example of a system 100 for automatic determination of a biological condition of a subject from ferning patterns. The system 100 includes an optical assembly 102 comprising at least one lens. In one implementation, the optical assembly 102 includes a light source, such as an LED light, a power source for the light source, a photosensor, and optical components to direct illumination from the light source to a specimen and magnify a resulting image of the specimen at the photosensor. It will be appreciated, however, that the system 100 can be designed to utilize ambient lighting, making any light source unnecessary.

In another implementation, the optical assembly can be located contained within a housing configured to engage with the mobile device such that an axis of the optical assembly is substantially aligned with a camera of a mobile device. In one implementation, the housing can include a plurality of leg members configured to space the optical assembly 102 from the camera by a focal length of the at least one lens. In another implementation, the housing can include extensions on opposite sides of the device to mechanically affix the optical assembly 102 and housing to the mobile device. In this implementation, the assembly 100 can utilize the camera, and potentially one or more light sources, from the smart phone, and the optical assembly 102 can include one or more optical components configured to direct illumination to the fluid sample and magnify the resulting image for the smart phone camera.

The optical assembly 102 can be configured to receive a microfluidic device 104 configured to hold a thin film of dried fluid. In one implementation, the device can be paired with a smearing block that is configured to transition along a channel in the microfluidic device 104 and provide a thin film of fluid across the surface of the channel. The microfluidic device 104 is configured to engage with the optical assembly 102 such that the dried fluid is aligned with an axis of the optical assembly. Accordingly, when the microfluidic device 104 is in place, the light source will provide transillumination to the dried fluid sample, and the resulting light will be focused by the at least one lens onto the photodetector or camera. Captured images of the fluid sample can then be used for analysis.

The captured images are provided to a computer vision model 106. The computer vision model 106 determines, from the preprocessed images of the fluid sample, at least one output value representing the presence or absence of the biological condition for the subject. It will be appreciated that, when the optical assembly 102 does not include a light source and relies upon ambient light, the computer vision model 106 can be trained to function in varying light conditions. In general, the computer vision model 106 will include a feature extractor that extracts a plurality of features indicative of the ferning pattern from a received image as continuous or categorical values, and at least one pattern recognition algorithm. The feature extractor can utilize any of a number of image processing techniques to generate a set of these values representing the content of the image, referred to as a feature vector.

In one example, one or more pattern recognition algorithms, such as classification or regression models, each analyze the extracted feature vector to assign a value to the user representing the biological condition. It will be appreciated that the value can be categorical or continuous. Where multiple classification and regression models are used, the computer vision model 106 can include an arbitration element can be utilized to provide a coherent result from the various algorithms. Depending on the outputs of the various models, the arbitration element can simply select a class from a model having a highest confidence, select a plurality of classes from all models meeting a threshold confidence, select a class via a voting process among the models, or assign a numerical parameter based on the outputs of the multiple models. Alternatively, the arbitration element can itself be implemented as a classification model that receives the outputs of the other models as features and generates one or more output classes for the patient.

The computer vision model 106, as well as any constituent models, can be trained on training data representing the various classes of interest. The training process of the computer vision model 106 will vary with its implementation, but training generally involves a statistical aggregation of training data into one or more parameters associated with the output classes. Any of a variety of techniques can be utilized for the models, including support vector machines, regression models, self-organized maps, k-nearest neighbor classification or regression, fuzzy logic systems, data fusion processes, boosting and bagging methods, rule-based systems, or artificial neural networks.

For example, an SVM classifier can utilize a plurality of functions, referred to as hyperplanes, to conceptually divide boundaries in the N-dimensional feature space, where each of the N dimensions represents one associated feature of the feature vector. The boundaries define a range of feature values associated with each class. Accordingly, an output class and an associated confidence value can be determined for a given input feature vector according to its position in feature space relative to the boundaries. An SVM classifier utilizes a user-specified kernel function to organize training data within a defined feature space. In the most basic implementation, the kernel function can be a radial basis function, although the systems and methods described herein can utilize any of a number of linear or non-linear kernel functions.

An ANN classifier comprises a plurality of nodes having a plurality of interconnections. The values from the feature vector are provided to a plurality of input nodes. The input nodes each provide these input values to layers of one or more intermediate nodes. A given intermediate node receives one or more output values from previous nodes. The received values are weighted according to a series of weights established during the training of the classifier. An intermediate node translates its received values into a single output according to a transfer function at the node. For example, the intermediate node can sum the received values and subject the sum to a binary step function. A final layer of nodes provides the confidence values for the output classes of the ANN, with each node having an associated value representing a confidence for one of the associated output classes of the classifier.

A k-nearest neighbor model populates a feature space with labelled training samples, represented as feature vectors in the feature space. In a classifier model, the training samples are labelled with their associated class, and in a regression model, the training samples are labelled with a value for the dependent variable in the regression. When a new feature vector is provided, a distance metric between the new feature vector and at least a subset of the feature vectors representing the labelled training samples is generated. The labelled training samples are then ranked according to the distance of their feature vectors from the new feature vector, and a number, k, of training samples having the smallest distance from the new feature vector are selected as the nearest neighbors to the new feature vector.

In one example of a classifier model, the class represented by the most labelled training samples in the k nearest neighbors is selected as the class for the new feature vector. In another example, each of the nearest neighbors can be represented by a weight assigned according to their distance from the new feature vector, with the class having the largest aggregate weight assigned to the new feature vector. In a regression model, the dependent variable for the new feature vector can be assigned as the average (e.g., arithmetic mean) of the dependent variables for the k nearest neighbors. As with the classification, this average can be a weighted average using weights assigned according to the distance of the nearest neighbors from the new feature vector. It will be appreciated that k is a metaparameter of the model that is selected according to the specific implementation. The distance metric used to select the nearest neighbors can include a Euclidean distance, a Manhattan distance, or a Mahalanobis distance.

A regression model applies a set of weights to various functions of the extracted features, most commonly linear functions, to provide a continuous result. In general, regression features can be categorical, represented, for example, as zero or one, or continuous. In a logistic regression, the output of the model represents the log odds that the source of the extracted features is a member of a given class. In a binary classification task, these log odds can be used directly as a confidence value for class membership or converted via the logistic function to a probability of class membership given the extracted features.

A rule-based classifier applies a set of logical rules to the extracted features to select an output class. Generally, the rules are applied in order, with the logical result at each step influencing the analysis at later steps. The specific rules and their sequence can be determined from any or all of training data, analogical reasoning from previous cases, or existing domain knowledge. One example of a rule-based classifier is a decision tree algorithm, in which the values of features in a feature set are compared to corresponding threshold in a hierarchical tree structure to select a class for the feature vector. A random forest classifier is a modification of the decision tree algorithm using a bootstrap aggregating, or "bagging" approach. In this approach, multiple decision trees are trained on random samples of the training set, and an average (e.g., mean, median, or mode) result across the plurality of decision trees is returned. For a classification task, the result from each tree would be categorical, and thus a modal outcome can be used, but a continuous parameter can be computed according to a number of decision trees that select a given task.

In one example, the computer vision model 106 can be implemented as a convolutional neural network that is trained on a plurality of images of dried fluid samples that have been classified as coming from ovulating subjects or non-ovulating subjects by one or more human experts. A convolutional neural network is a feed-forward artificial neural network that includes convolutional layers, which effectively apply a convolution to the values at the preceding layer of the network to emphasize various sets of features within an image. In a convolutional layer, each neuron is connected only to a proper subset of the neurons in the preceding layer, referred to as the receptive field of the neuron. Accordingly, the convolutional neural network can perform both the feature extraction and the classification functions for the computer vision model 106. In one implementation, at least one chromatic value (e.g., a value for an RGB color channel, a YCrCb color channel, or a grayscale brightness) associated with each pixel is provided as an initial input to the convolutional neural network.

It will be appreciated that the computer vision model 106 can be implemented as software instructions stored on a non-transitory computer readable medium and executed by an associated processor. In one implementation, the computer vision model 106 can be implemented on a cloud computing system or other remote server that is accessed by the system 100 via a network connection. In another implementation, the computer vision model 106 is stored locally at the system, for example, on a memory of a mobile device or a microprocessor integrated into the system. The computer vision model 106 can contain fully connected layers as well as convolutional and pooling layers, and in one implementation, the network will have at least three convolutional layers followed by one or more fully connected layers.

The results of the classification at the computer vision model 106 can be provided to a user at an associated user interface 108. For example, the user interface 108 can include at least an output device, such as a display, and appropriate software, stored on a non-transitory medium and executed by an associated processor, for receiving the output of the convolutional neural network 106 and presenting it at the output device. Where the system 100 is configured to utilize a mobile device, the user interface 108 can be a touchscreen associated with the mobile device.

Figure 2:
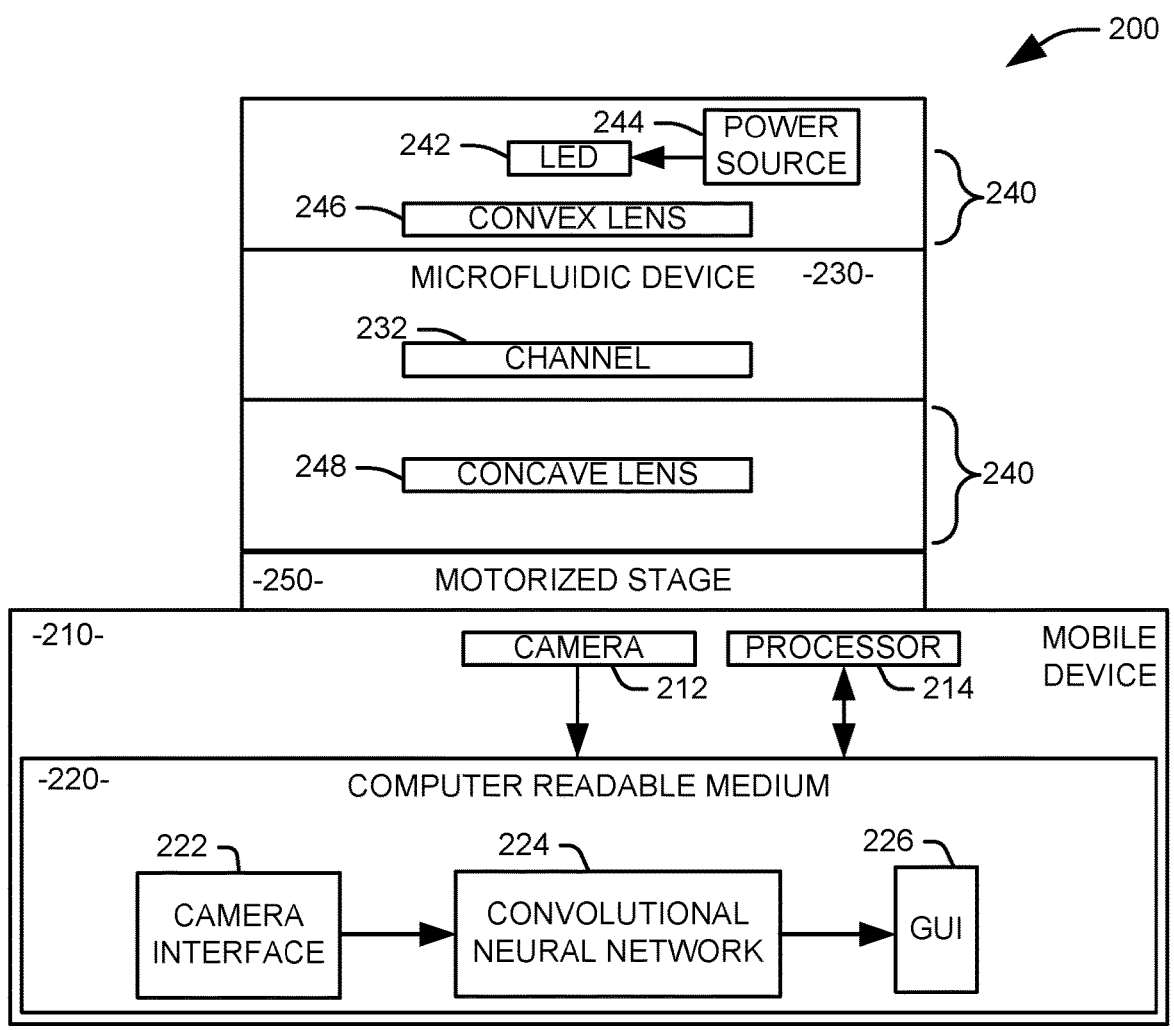
FIG. 2 illustrates one implementation of a system for determining if a subject is ovulating from a saliva sample.

FIG. 2 illustrates one implementation of a system 200 for determining if a subject is ovulating from a saliva sample. In the illustrated implementation, the illustrated system 200 is used with a mobile device 210 comprising a camera 212, a processor 214, and a non-transitory computer readable medium 220 that stores machine executable instructions 222, 224, and 226 for receiving and processing images from the camera 212. The system 200 in combination with the mobile device 210 provides a point-of-care ovulation evaluation system that is easy-to-use, rapid, and inexpensive.

Figure 3:
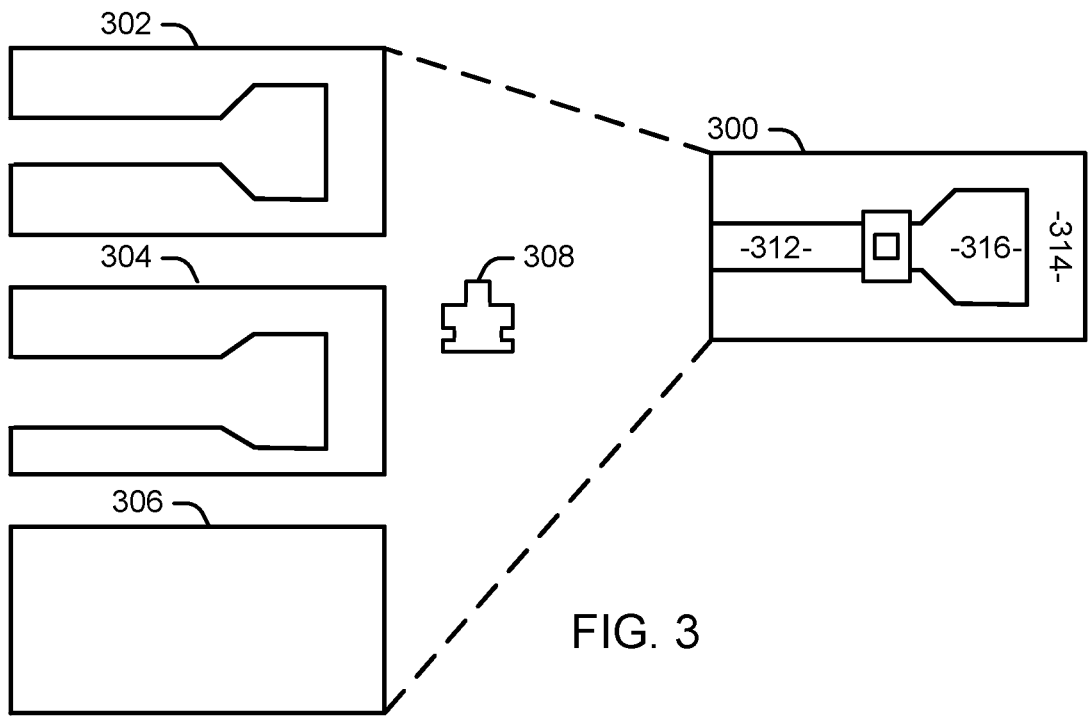
FIG. 3 illustrates one example of a microfluidic device that could be used in the system of FIG. 2.

A microfluidic device 230 is configured to hold a saliva sample from a subject. In the illustrated example, the microfluidic device 230 contains a channel 232 across which a saliva sample can be spread to dry, allowing the ferning pattern to develop. FIG. 3 illustrates one example of a microfluidic device 300 that could be used in the system 200 of FIG. 2. In one implementation, the microfluidic device 300 is formed from a first layer 302 of poly(methyl methacrylate) (PMMA), a second layer 304 of double-sided adhesive, and a glass slide 306. The PMMA layer is 302 etched to create grooves, such that the inner side of the fully built microfluidic device 300 would act as guideways for a smearer block 308 that generates a thin, uniform layer of saliva within a channel 312. A small area 314 is left open on one end of the glass slide for handling the microfluidic device. One side of layer 304 of double-sided adhesive was stuck to the etched groove side of the PMMA layer 302 and the other side was stuck to the glass slide 306, which was used as the lower substrate for the device. The smearer block 308 can be formed from polylactic acid, and in one example, can be printed using a 3-D printer with polylactic acid as the printing material. The smearer block 308 is used to smear the saliva sample within the channel 312 of the microfluidic device to get a controlled thin film of saliva. The microfluidic device 300 also includes a small reservoir 316 for loading the sample onto the device.

Returning to FIG. 2, an optical assembly 240 that includes a light-emitting diode (LED) 242 configured to illuminate a sample inserted into the optical assembly 240. The LED 242 can be powered by either a power source 244 placed within the housing, such as a watch battery, or through a battery associated with the mobile device 210. The optical assembly 240 further includes a plurality of lenses 246 and 248. In the illustrated implementation, a first lens 246 is positioned between the LED 242 and the channel 232 in the microfluidic device 230 and a second lens 248 is positioned near an aperture of the optical assembly 240, between the channel 232 and the camera 212 of the mobile device 210. In the illustrated example, the first lens 246 is an acrylic lens with a twelve-millimeter diameter and a thirty-millimeter focal length used as a condenser lens and the second lens 248 is a plano-convex lens with a diameter of nine millimeters and a focal length of 13.5 millimeters for magnification of the saliva sample. The first lens 246 and the second lens 248 are positioned as to focus light from the light source through the channel and into aperture, with the lenses and the aperture defining an optical axis of the optical system.

In the illustrated implementation, the optical assembly 240 is housed in a 3-D printed, biodegradable Polylactic Acid (PLA) housing. In one example, the printed assembly weighs approximately twenty grams, not including the battery, and measures around 8×9×7 centimeters. The housing is configured such that the lenses are aligned with a rear camera of the mobile device and, when the housing is in place, the lenses 246 and 248 are fixed in place at a distance appropriate for the focal length of the lenses. The cellphone's auto focus is utilized to achieve fine focusing.

The system 200 further includes a motorized stage 250 for moving the microfluidic device 230 relative to the remainder of the assembly 200. The motorized stage 250 translates the microfluid device 230 along a single axis within a focal plane of the second lens 238 to automate the imaging of the microfluidic channel. The microfluidic device 230 was optimally focused by placing the device at the working distance of the lens setup, which helped eliminating manual focusing by the user. In one example, the motorized stage 250 includes a 6 V, 100 rpm DC gear motor with a M3 lead screw attached to the shaft, and a single-board microcontroller used to control movement of the microfluidic device.

The non-transitory computer readable medium 220 stores executable instructions 222, 224, and 226 for determining if a subject is ovulating from images or video captured at the camera 212. The software application was designed to provide a user-friendly interface for determining the presence or absence of ovulation. The application lets the user to take images for analysis as well as archive previous tests and their reports. A camera interface 222 is configured to instruct the camera 212 to capture the images or video. It will be appreciated that this can be done in concert with the analysis of the dried saliva sample, such that the analysis is performed substantially in real-time, or a recording can be stored for later analysis. The camera interface 222 can also resize all of the images captured at the camera 212 to a standard size for analysis and apply any image processing techniques that may be desirable for enhancing the quality of the image for analysis.

In one example, when a microfluidic device with a loaded sample was inserted into the optical attachment, the camera interface 222 can instruct the motorized stage 250 to translate the microfluidic device in parallel to the second lens 248 to image the entire channel for salivary ferning automatically. In one example, the camera interface can control the motors via wireless communication between the smartphone and the motorized stage. The camera interface 222 can instruct the camera to capture video frames of the microchannel at a rate of around five frames per second (fps), covering an area of 2.1×22.6 mm$^2$ of the microfluidic device in less than thirty-one seconds per sample.

The images from the camera interface 222 are provided to a convolutional neural network 224 that determines, from the preprocessed images of the saliva sample, if the subject is ovulating. For example, the convolutional neural network 224 can classify the image as a binary classification into "ovulating" or "not ovulating" classes, one of a plurality of classes representing ranges of likelihoods that the subject is ovulating, or assign a continuous value representing the likelihood that the subject is ovulating. It will be appreciated that, in one implementation, a subject can be determined to be ovulating if the ferning pattern is detected in any of the captured frames comprising the video.

The illustrated convolutional neural network 224 utilizes depth-wise separable convolutions to provide a lightweight, deep neural network, as opposed to more traditional convolution neural network that primarily uses simple convolution. A simple convolution applies a convolution kernel to all channels of the input image. Simple convolution slides the kernels across all input image channels and computes a weighted sum of input pixels, according to the applied kernel, for all input channels. Depth-wise convolution is a spatial separable convolution performed on separate channels whose output is computed into a new channel by a pointwise convolution, equivalent to a standard convolution with the 1×1 kernel. It will be appreciated that a given pointwise convolution can apply multiple 1×1 kernels across a plurality of channels in the network to provide a plurality of channels for the output.

In the illustrated implementation, a first convolutional layer applies a standard 3×3 convolution, with a plurality of additional convolutional layers that apply depth-wise convolutions. In one example, the convolutional neural network 224 can include thirteen convolutional layers, each comprising a depth-wise convolution, followed by a pointwise convolution. Each convolutional layer is followed by a rectified linear unit (ReLU) and batch normalization. The last layer is an average pooling layer that reduces the spatial resolution to one followed by a fully connected layer that is fed to a classification layer for detection. Down sampling was addressed with strided convolution in the depth-wise convolutions as well as in the first layer. The classification layer was added at the end and was trained to classify the saliva samples into ovulating and non-ovulating based on the ferning patterns. In practice, a transfer learning technique can be used to reduce the amount of training data necessary for the convolutional neural network, with a set of pre-trained weights from an existing convolutional neural network used to provide feature extraction from the convolutional layers. Accordingly, only the classification layer was trained with labelled training data from ovulating and non-ovulating subjects.

A graphical user interface (GUI) 226 is configured to provide the results from the convolutional neural network 224 to the user via a display of the mobile device 210. For example, the GUI 226 can provide an indication as to whether a subject whose saliva samples are represented in the images is currently ovulating. In addition to an option to begin real-time analysis of a sample, the GUI 226 can provide an option where videos pre-recorded with the cellphone attachment can be analyzed and an option where the user can access the test history. The GUI 226 can also provide a questionnaire where general information about the subject is obtained prior to testing.

Figure 4:
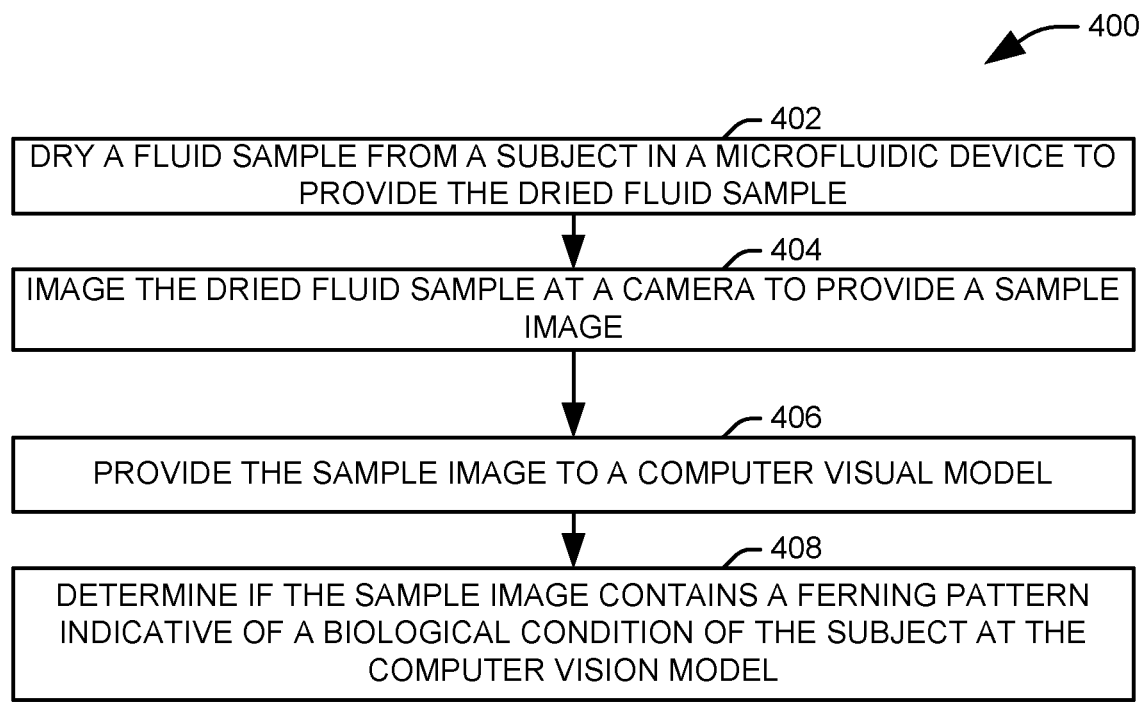
FIG. 4 illustrates one example of a method for automatic determination of a biological condition of a subject from ferning patterns.

In view of the foregoing structural and functional features described above in FIGS. 1-3, example methods will be better appreciated with reference to FIG. 4. While, for purposes of simplicity of explanation, the method of FIG. 4 are shown and described as executing serially, it is to be understood and appreciated that the present invention is not limited by the illustrated order, as some actions could in other examples occur in different orders and/or concurrently from that shown and described herein.

FIG. 4 illustrates one example of a method 400 for automatic determination of a biological condition of a subject from ferning patterns in a dried fluid sample. At 402, a fluid sample from a subject in a microfluidic device to provide the dried fluid sample. In one example, the fluid sample is deposited in a reservoir on the microfluidic device and the fluid sample in spread in a thin layer across a channel of the microfluidic device using a smearer block. At 404, the dried fluid sample is imaged at a camera to provide a sample image. In one example, the sample image is obtained by attaching an optical assembly to a mobile device, inserting the microfluidic device into the optical assembly, and capturing an image of the dried fluid sample at the camera. It will be appreciated that multiple images can be captured for analysis, for example, by translating the microfluidic device in a direction parallel to the plane of the camera and capturing video of the dried fluid sample at a camera of the mobile device.

At 406, the sample image is provided to a computer vision model. In one example, the computer vision model is stored on a non-transitory computer readable medium local to the camera. In another example, the computer vision model is stored on remote server, and the sample image is provided to the computer vision model via a network interface. In one implementation, the computer vision model is implemented as a convolutional neural network. At 408, it is determined, at the computer vision model, if the sample image contains a ferning pattern indicative of a biological condition of the subject. In one example, in which the fluid sample is a saliva sample, the computer vision model determines if the subject is ovulating from the sample image.

Figure 5:
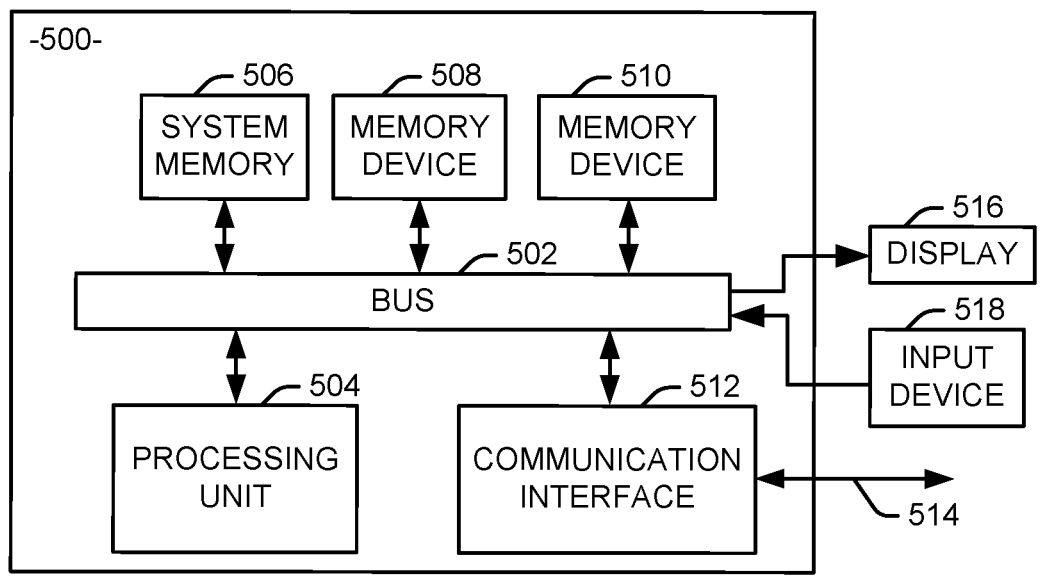
FIG. 5 is a schematic block diagram illustrating an exemplary system of hardware components capable of implementing examples of the systems and methods disclosed in FIGS. 1-4.

FIG. 5 is a schematic block diagram illustrating an exemplary system 500 of hardware components capable of implementing examples of the systems and methods disclosed in FIGS. 1-4. The system 500 can include various systems and subsystems. The system 500 can be a personal computer, a laptop computer, a workstation, a computer system, an appliance, an application-specific integrated circuit (ASIC), a server, a server blade center, a server farm, etc.

The system 500 can includes a system bus 502, a processing unit 504, a system memory 506, memory devices 508 and 510, a communication interface 512 (e.g., a network interface), a communication link 514, a display 516 (e.g., a video screen), and an input device 518 (e.g., a keyboard and/or a mouse). The system bus 502 can be in communication with the processing unit 504 and the system memory 506. The additional memory devices 508 and 510, such as a hard disk drive, server, stand-alone database, or other non-volatile memory, can also be in communication with the system bus 502. The system bus 502 interconnects the processing unit 504, the memory devices 506-510, the communication interface 512, the display 516, and the input device 518. In some examples, the system bus 502 also interconnects an additional port (not shown), such as a universal serial bus (USB) port.

The processing unit 504 can be a computing device and can include an application-specific integrated circuit (ASIC). The processing unit 504 executes a set of instructions to implement the operations of examples disclosed herein. The processing unit can include a processing core.

The additional memory devices 506, 508 and 510 can store data, programs, instructions, database queries in text or compiled form, and any other information that can be needed to operate a computer. The memories 506, 508 and 510 can be implemented as computer-readable media (integrated or removable) such as a memory card, disk drive, compact disk (CD), or server accessible over a network. In certain examples, the memories 506, 508 and 510 can comprise text, images, video, and/or audio, portions of which can be available in formats comprehensible to human beings. Additionally or alternatively, the system 500 can access an external data source or query source through the communication interface 512, which can communicate with the system bus 502 and the communication link 514.

In operation, the system 500 can be used to implement one or more parts of a system for automatically determining a biological condition of a subject from ferning patterns in accordance with the present invention. Computer executable logic for implementing the system resides on one or more of the system memory 506, and the memory devices 508, 510 in accordance with certain examples. The processing unit 504 executes one or more computer executable instructions originating from the system memory 506 and the memory devices 508 and 510. The term "computer readable medium" as used herein refers to a medium that participates in providing instructions to the processing unit 504 for execution and can include multiple discrete physical units.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications, and variations that fall within the scope of the appended claims.

What is claimed is:

1. A system comprising:
    an optical assembly comprising at least one lens and having an associated axis;
    a microfluidic device comprising a channel to hold a fluid sample from a subject and configured to engage with the housing such that the channel is aligned with the axis of the optical assembly;
    a camera aligned with the axis of the optical assembly;
    a processor; and
    a non-transitory computer readable medium storing executable instructions for providing at least one image captured at the camera to a computer vision model to determine if there is a ferning pattern representative of a biological condition of the subject in the at least one image, the computer vision model being implemented as a convolutional neural network, comprising:
        a plurality of convolutional layers, each applying a depth-wise convolution kernel to each of a plurality of channels within the network and a point-wise convolution that applies a one-by-one kernel across all of the plurality of channels within the network;
        a fully connected layer that is connected to a last of the plurality of convolutional layers; and
        a classification layer that is connected to the fully connected layer.

2. The system of claim 1, wherein the fluid is salvia and the computer vision model determines if the subject is ovulating.

3. The system of claim 1, wherein the fluid is amniotic fluid and the computer vision model determines if the subject has experienced premature rupture of membranes during pregnancy.

4. The system of claim 1, wherein the fluid is ocular tear film and the computer vision model determines if the subject has dry eye syndrome.

5. The system of claim 1, the microfluidic device comprising a reservoir for receiving the fluid sample, the channel being configured to receive a smearing block that spreads a thin film of the fluid sample across the channel.

6. The system of claim 1, wherein each of the camera, the processor, and the non-transitory computer readable medium are part of a mobile device, the optical assembly being deployed with a housing configured to attach to the mobile device such that the camera is aligned with the axis of the optical assembly and the housing being configured to receive the microfluidic device such that the channel is aligned with the axis of the optical assembly.

7. The system of claim 6, further comprising a user interface that displays the output of the computer vision model on a display of the mobile device.

8. The system of claim 1, wherein the optical assembly includes a light source, and the at least one lens includes a first lens, positioned between the light source and the channel, to direct illumination to the fluid sample, and a second lens, positioned between the fluid sample and the camera, to magnify an image of the fluid sample at the camera.

9. A method comprising:
    air-drying a fluid sample from a subject in a microfluidic device to provide a dried fluid sample having an associated ferning pattern;
    imaging the dried fluid sample at a camera to provide a sample image containing the ferning pattern;
    providing the sample image to a computer vision model; and
    determining, at the computer vision model, if the ferning pattern is indicative of a biological condition of the subject, wherein determine if the ferning pattern is indicative of the biological condition at the computer vision model comprises providing the sample image to a convolutional neural network that applies, at each of a plurality of convolutional layers, a depth-wise convolution kernel to each of a plurality of channels within the network and a point-wise convolution that applies a one-by-one kernel across all of the plurality of channels within the network.

10. The method of claim 9, wherein drying the fluid sample in the microfluidic device comprises depositing the fluid sample in a reservoir on the microfluidic device and spreading the fluid sample in a thin layer across a channel of the microfluidic device using a smearer block.

11. The method of claim 9, wherein imaging the dried fluid sample comprises:
    attaching an optical assembly to a mobile device, the mobile device including the camera;
    inserting the microfluidic device into the optical assembly; and
    capturing an image of the dried fluid sample at the camera.

12. The method of claim 9, wherein imaging the dried fluid sample comprises translating the microfluidic device in a direction parallel to the plane of the camera and capturing video of the dried fluid sample at the camera.

13. The method of claim 9, wherein the fluid sample is a saliva sample, determining, at the computer vision model, if the sample image contains the ferning pattern indicative of the biological condition of the subject, comprises determining if the subject is ovulating.

14. The method of claim 9, wherein providing the sample image to the computer vision model comprises providing the sample image to a computer vision model stored on a non-transitory computer readable medium local to the camera.

15. The method of claim 9, wherein providing the sample image to the computer vision model comprises providing the sample image to a computer vision model stored on remote server via a network interface.

16. A system comprising:
    an optical assembly comprising at least one lens;
    a microfluidic chip comprising a channel to hold a thin layer of a saliva sample from a subject and configured to engage with the optical assembly such that the reservoir is aligned with the optical axis of the optical assembly, the channel being configured such that the thin layer of the fluid sample forms a ferning pattern via air drying; and
    a mobile device, comprising:

a camera aligned along the optical axis of the optical assembly;
a processor; and
a non-transitory computer readable medium storing executable instructions for determining if the subject is ovulating from images captured at the camera, the executable instructions comprising:
   a camera interface configured to instruct the camera to capture the images;
   a convolutional neural network that determines if the ferning pattern is representative of ovulation by the subject in the at least one image, the convolutional neural network comprising:
   a plurality of convolutional layers, each applying a depth-wise convolution kernel to each of a plurality of channels within the network and a point-wise convolution that applies a one-by-one kernel across all of the plurality of channels within the network;
   a fully connected layer that is connected to a last of the plurality of convolutional layers; and
      a classification layer that is connected to the fully connected layer; and
   a user interface that displays the output of the convolutional neural network on a display of the mobile device.

17. The system of claim 16, wherein the optical assembly is housed in a three-dimensional (3-D) printed plastic housing.

* * * * *